US010603342B2

(12) United States Patent
Carreras et al.

(10) Patent No.: US 10,603,342 B2
(45) Date of Patent: Mar. 31, 2020

(54) LACTIC ACID BACTERIA FOR COELIAC DISEASE

(71) Applicant: Compagnie Gervais Danone, Paris (FR)

(72) Inventors: Agusti Montserrat Carreras, Barcelona (ES); Montserrat Andreu Corominas, Barcelona (ES); Daniel Ramon Vidal, Valencia (ES); Salvador Genoves Martinez, Valencia (ES); Esther Bataller Leiva, Valencia (ES)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 15/287,187

(22) Filed: Oct. 6, 2016

(65) Prior Publication Data

US 2017/0145379 A1    May 25, 2017

Related U.S. Application Data

(63) Continuation of application No. 13/634,458, filed as application No. PCT/IB2010/000699 on Mar. 12, 2010, now abandoned.

(51) Int. Cl.
| | | |
|---|---|---|
| *A61K 35/74* | (2015.01) | |
| *A61K 35/744* | (2015.01) | |
| *C12R 1/225* | (2006.01) | |
| *C12R 1/46* | (2006.01) | |
| *C12R 1/245* | (2006.01) | |
| *C12N 1/20* | (2006.01) | |
| *A61K 35/747* | (2015.01) | |
| *C12N 1/18* | (2006.01) | |
| *C12Q 1/02* | (2006.01) | |

(52) U.S. Cl.
CPC ............ *A61K 35/74* (2013.01); *A61K 35/744* (2013.01); *A61K 35/747* (2013.01); *C12N 1/18* (2013.01); *C12N 1/20* (2013.01); *C12Q 1/02* (2013.01); *C12R 1/225* (2013.01); *C12R 1/245* (2013.01); *C12R 1/46* (2013.01)

(58) Field of Classification Search
CPC .... A61K 35/74; A61K 35/744; A61K 35/747; C12N 1/18; C12N 1/20; C12Q 1/02; C12R 1/225; C12R 1/245; C12R 1/46
See application file for complete search history.

(56) References Cited

U.S. PATENT DOCUMENTS 8,137,952 B2    3/2012 Hakansson et al.

FOREIGN PATENT DOCUMENTS

WO    2010/1043696 A1    4/2010

OTHER PUBLICATIONS

Habibi-Najafi et al.., 1994, J Dairy Sci., vol. 77, pp. 385-392.*
De Vuyst et al., Trends in Food Science & Technology 16 (2005) 43-56.*
Spanhaak et al., European Journal of Clinical Nutrition (1998) 52, 899-907.*
De Angelis et al., "VSL#3 probiotic preparation has the capacity to hydrolyze gliadin polypeptides responsible for Celiac Sprue," Biochimica et Biophysica Acta, 1762: 80-93 (2006).
Di Cagno et al., "Proteolysis by Sourdough Lactic Acid Bacteria: Effects on Wheat Flour Protein Fractions and Gliadin Peptides Involved in Human Cereal Intolerance," Applied and Environmental Microbiology, 68: 623-533 (2002).
Di Cagno et al., "Sourdough Bread Made from Wheat and Nontoxic Fours and Started with Selected Lactobacilli Is Tolerated in Celiac Sprue Patients," Applied and Environmental Microbiology, 70: 1088-1096 (2004).
Fiori, "Role of LAB petidases in the hydrolysis of antigenic gliadins and gliadin-like fragment deriving from the 33-mer peptide," 14th Workshop on the Developments in the Italian PhD Research on Food Science Technology and Biotechnology—University of Sassari Oristano, Sep. 16-18, 2009.
Gerez et al., "Functionality of lactic acid bacteria peptidase activities in the hydrolysis of gliadin-like fragments," Letters in Applied Microbiology, 47: 427-432 (2008).
Gobbetti et al., "Sourdough lactobacilli and celiac disease," Food Microbiology, 24: 187-196 (2007).
Granato et al., "Cell Surface-Associated Elongation Factor Tu Mediates the Attachment of Lactobacillus johnsonii (NCC533 (La1) to Human Intestinal Cells and Mucins," Infection and Immunity, 72: 2160-2169 (2004).
Laparra et al., "Bifidobacteria Inhibit the Inflammatory Response Induced by Gliadins in Intestinal Epithelial Cells via modifications of Toxic Peptide Generation During Digestion," Journal of Cellular Biochemistry, 109: 801-807 (2010).
Mamone et al., "Susceptibility to transglutaminase of gliadin peptides predicted by a mass spectrometry-based assay," FEBS Letters, 562: 177-182 (2004).
Rizzello et al., "Highly Efficient Gluten Degradation by Lactobacilli and Fungal Proteases during Food Processing: New Perspectives for Celiac Disease," Applied and Environmental Microbiology, 73: 4499-4507 (2007).
Rollan et al., "Proteolytic activity and reduction of gliadin-like fractions by sourdough lactobacilli," Journal of Applied Microbiology, 99: 1495-1502 (2005).
International Search Report issued in PCT/IB2010/000699 dated Dec. 22, 2010.

* cited by examiner

Primary Examiner — Deborah K Ware
(74) Attorney, Agent, or Firm — Morgan, Lewis & Bockius LLP

(57) ABSTRACT

The present invention discloses strains of *Lactobacillus* and *Streptococcus* which have a capacity to degrade gliadin peptides involved in coeliac disease and which peptide degrading activity is stable under low pH and in the presence of mammalian digestive enzymes. These strains are suitable in a product for use in prevention and/or treatment of celiac disease.

2 Claims, No Drawings

Specification includes a Sequence Listing.

SEQUENCE LISTING

<160> NUMBER OF SEQ ID NOS: 4

<210> SEQ ID NO 1
<211> LENGTH: 33
<212> TYPE: PRT
<213> ORGANISM: Artificial Sequence
<220> FEATURE:
<223> OTHER INFORMATION: 33-mer peptide

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro

```
                    20              25              30
Phe

<210> SEQ ID NO 2
<211> LENGTH: 20
<212> TYPE: PRT
<213> ORGANISM: Artificial Sequence
<220> FEATURE:
<223> OTHER INFORMATION: 20-mer peptide

<400> SEQUENCE: 2

Gln Gln Leu Pro Gln Pro Gln Gln Pro Gln Gln Ser Pro Phe Gln Gln
1               5                   10                  15

Gln Arg Pro Phe
            20

<210> SEQ ID NO 3
<211> LENGTH: 13
<212> TYPE: PRT
<213> ORGANISM: Artificial Sequence
<220> FEATURE:
<223> OTHER INFORMATION: 13-mer peptide

<400> SEQUENCE: 3

Leu Gly Gln Gln Gln Pro Phe Pro Pro Gln Gln Pro Tyr
1               5                   10

<210> SEQ ID NO 4
<211> LENGTH: 18
<212> TYPE: PRT
<213> ORGANISM: Artificial Sequence
<220> FEATURE:
<223> OTHER INFORMATION: 18-mer peptide

<400> SEQUENCE: 4

Pro Gln Leu Pro Tyr Pro Gln Pro Gln Leu Pro Tyr Pro Gln Pro Gln
1               5                   10                  15

Pro Phe
```

LACTIC ACID BACTERIA FOR COELIAC DISEASE

SEQUENCE LISTING SUBMISSION VIA EFS-WEB

A computer readable text file, entitled "SequenceListing.txt," created on or about 12 Sep. 2012 with a file size of about 2 kb contains the sequence listing for this application and is hereby incorporated by reference in its entirety.

FIELD

The invention relates to lactobacilli or streptococci in the treatment or prevention of coeliac disease.

BACKGROUND ART

Coeliac disease is an autoimmune disorder of the small intestine that occurs in genetically predisposed people of all ages from infancy on up. Coeliac disease is caused by a reaction to gliadins, a family of related proline and glutamine rich protein in gluten protein, which are found in wheat (and similar proteins of the tribe Triticeae, such as barley and rye). Upon exposure to gliadin, the enzyme tissue transglutaminase modifies the protein, and the immune system of subjects prone to celiac disease reacts and cross-reacts with the small-bowel tissue, causing an inflammatory reaction. The inflammation subsequently leads to villous atrophy and interferes with the absorption of nutrients, including minerals and fat soluble vitamins. Classic symptoms of coeliac disease include abdominal distension, vomiting, diarrhoea, weight loss (or stunted growth in children), anaemia and fatigue. The strongest and most common response of the immune system to gliadin is directed toward an α2-gliadin fragment of 33 amino acids in length (represented herein as SEQ ID NO: 1) (Shan et al. 2005 J. Proteome Res. 4:1732-1741; Moron et al. 2008; Am. J. Clin. Nut 87(2): 405-14).

The prevalence of clinically diagnosed coeliac disease is 0.05-0.27%. However, population studies from parts of Europe, India, South America, Australasia and the USA indicate that the prevalence may be between 0.33 and 1.06% in children and 0.18-1.2% in adults. There are indications that many people are undiagnosed and have only mild symptoms of gastro-intestinal discomfort.

The only known effective treatment so far is a lifelong gluten-free diet.

A combination of enzymes (prolyl endopeptidase and a barley glutamine-specific cysteine endopeptidase (EP-B2)) that degrade the putative 33-mer peptide epitope of α2-gliadin in the duodenum is disclosed by Siegel M. et al. (2006, Chem Biol 13 (6): 649-58). Piper et al. (2004, J Pharm Exper. Therap 311: 213-219) disclose the use of prolyl-endopeptidase to degrade gliadin peptides. WO 2007/108763 discloses Lactobacillus plantarum strains and a Lactobacillus rhamnosus strain for promoting immunetolerance in coeliac disease or atopic dermatitis. WO 2006/097415 discloses a mixture of 8 sourdough lactic acid bacteria and Bifidobacteria capable of degrading gliadins peptides, such as the fragment 62-75 of the A-gliadin and the epitope 33-mer peptide, thanks to a complementary proteolytic activity between the bacteria. Baked food obtained from these lactic acid bacteria and Bifidobacteria can be used in the diet of a subject suffering from celiac disease. WO 03/028745 discloses strains of lactic acid bacteria with internal peptidases capable of degrading exorphin A5, a 5-mer peptide derived from gluten protein. These strains are capable of lowering the concentration of intestinal pathogenic peptides.

SUMMARY OF THE INVENTION

In vitro studies were carried out in order to select strains of lactic acid bacteria with probiotics characteristics. A large number of strains belonging to the genera Lactobacillus, Streptococcus or Bifidobacterium were screened for peptidase activity in the culture supernatant capable to degrade the 33-mer peptide LQLQPFPQPQLPYPQPQLPYPQPQLPYPQPQPF (SEQ ID NO: 1) that is involved in coeliac disease.

The initially selected strains were then screened for their ability to survive the gastro-intestinal tract and for the stability of the supernatant peptidase activity under gastro-intestinal tract, i.e. their ability to reach and still have an active 33-mer peptide degrading peptidase activity at the site of action for coeliac disease, i.e., the small intestine.

Subsequently the selected strains were tested for their ability to degrade other peptides assumed to be involved in coeliac disease, namely a 20-mer from α-gliadin QQLPQPQQPQQSPFQQQRPF (SEQ ID NO: 2) and 13-mer from A-gliadin, LGQQQPFPPQQPY (SEQ ID NO: 3).

Surprisingly it was found that the 33-mer peptide was slowly degraded under conditions mimicking the human digestive tract and that a 18-mer peptide breakdown product PQLPYPQPQLPYPQPQPF (SEQ ID NO: 4) emerged which was completely resistant against further degradation by human digestive enzymes. This novel finding enabled an improved further selection, by screening the lactic acid bacterial strains for their capacity to degrade the 18-mer peptide.

From a large number of strains, three single strains and a mixture of two strains were finally selected. These strains are resistant to gastrointestinal conditions, produce a high peptidase activity stable under gastro-intestinal conditions and advantageously degrade the 33-mer, the 20-mer, the 13-mer peptides involved in coeliac disease and also degrade the resistant 18-mer peptide. The enzyme responsible for the peptide degradation was purified from these strains and characterised, sequenced and was identified as a protein identical to the elongation factor Tu in the case of Lactobacillus casei and as an elongation factor G in the case of Streptococcus thermophilus.

Consumption of these specific strains of lactic acid bacteria or the enzymes produced by these bacteria with the peptidase activity therefore can be advantageously used in persons suffering from coeliac disease or in persons at risk at suffering from celiac disease, such as persons with a family history of celiac disease or persons with mild gastrointestinal problems associated with celiac disease. Preferably the strains are administered in a fresh, fermented product, more preferably a fermented dairy product.

DETAILED DESCRIPTION OF THE INVENTION

Accordingly, the present invention provides a strain of lactic acid bacterium and/or a medium fermented by a strain of lactic acid bacterium for use in treatment and/or prevention of coeliac disease, wherein said lactic acid bacterium and/or medium fermented by a lactic acid bacterium are capable to degrade the 33-mer peptide LQLQPFPQPQLPYPQPQLPYPQPQLPYPQPQPF (SEQ ID NO:

1), the 20-mer peptide QQLPQPQQPQQSPFQQQRPF (SEQ ID NO: 2), the 13-mer peptide LGQQQPFPPQQPY (SEQ ID NO: 3) and/or the 18-mer peptide PQLPYPQPQLPYPQPQPF (SEQ ID NO: 4), and wherein the lactic acid bacterium is selected from the group consisting of the genus *Lactobacillus* and *Streptococcus*.

In the preferred embodiment of the present invention, said lactic acid bacteria and/or wherein said medium fermented by said lactic acid bacteria are capable to degrade the 33-mer peptide of SEQ ID NO: 3 and the 18-mer peptide of SEQ ID NO: 4.

The present invention also provides a mixture of two strains of lactic acid bacteria and/or a medium fermented by a mixture of two strains of lactic acid bacteria for use in treatment and/or prevention of coeliac disease, wherein said lactic acid bacteria and/or medium fermented by lactic acid bacteria are capable to degrade the 33-mer peptide of SEQ ID NO: 1, the 20-mer peptide of SEQ ID NO: 2, the 13-mer peptide of SEQ ID NO: 3 and/or the 18-mer peptide of SEQ ID NO: 4, preferably the 33-mer peptide of SEQ ID NO: 3 and the 18-mer peptide of SEQ ID NO: 4, and wherein the lactic acid bacteria are selected from the group consisting of the genus *Lactobacillus* and *Streptococcus*.

The present invention also provides a composition comprising at least one strain selected from the group consisting of *Lactobacillus helveticus* CNCM I-4279, *L. delbrueckii* subsp *lactis* CNCM I-4280, *Lactobacillus casei* CNCM I-4270, *Streptococcus thermophilus* CNCM I-4269 and a mixture of *S. thermophilus* CNCM I-2776 and *L. bulgaricus* CNCM I-2787.

The present invention also provides the use of at least one strain of lactic acid bacteria selected from the group consisting of the genus *Lactobacillus* and *Streptococcus* that produce a protein elongation factor for degradation of the 33-mer peptide of SEQ ID NO: 1, the 20-mer peptide of SEQ ID NO: 2, the 13-mer peptide SEQ ID NO: 3 and/or the 18-mer peptide SEQ ID NO: 4, preferably the 33-mer peptide of SEQ ID NO: 3 and the 18-mer peptide of SEQ ID NO: 4.

The present invention also provides a method of selecting strains of lactic acid bacteria for use in treatment and/or prevention of coeliac disease comprising the steps of selecting the strains with the capacity of degrading the 18 mer peptide of SEQ ID NO: 4, when at least 45%, preferably at least 70%, of said peptide is hydrolyzed in the presence of a culture supernatant of said strains.

Coeliac Disease:

Coeliac disease, or celiac disease is also sometimes referred to as c(o)eliac sprue, non-tropical sprue, endemic sprue, gluten enteropathy, gluten-sensitive enteropathy, and gluten intolerance. The disease is diagnosed by a doctor as known in the art and involves serological blood tests and usually an endoscopy/gastroscopy and biopsy.

Coeliac disease is a disorder of the small intestine caused by a reaction to gliadins, a family of related proline and glutamine rich protein in gluten protein, found in wheat, barley and rye. Upon exposure to gliadin, the immune system causes an inflammatory reaction that leads to villous atrophy and interferes with the absorption of nutrients, including minerals and fat soluble vitamins. Coeliac disease patients often suffer from abdominal distension, vomiting, diarrhoea, weight loss (or stunted growth in children), anaemia and fatigue.

Lactic Acid Bacteria:

A lactic acid bacterium, a mixture of lactic acid bacteria or a media fermented by lactic acid bacteria according to the present invention is capable of degrading a peptide as defined above when at least 45%, and by order of increasing preference at least 50%, 55%, 60%, 65%, 70%, 75%, 80%, 85% and 90% of said peptide is hydrolyzed in the presence of a culture supernatant of a selected lactic acid bacteria or mixture of selected lactic acid bacteria.

The peptide degradation assay can be carried out by enzymatic proteolysis activity present in the culture supernatant of a selected lactic acid bacterium or a mixture of selected lactic acid bacteria obtained in logarithmic and stationary phase culture as follows: the assay is carried out with a mixture containing PBS (e.g. 100 mM, pH 7.3), the peptide (e.g., 1-2 mM) and the culture supernatant (e.g. 20-30 µl) for 48 hours at 37° C.; then the sample is boiled, filtered (e.g. through 0.45 µm) and analysed by high-performance liquid chromatography.

In vitro studies were carried out in order to select strains of lactic acid bacteria with these properties. A large number of strains belonging to the genera *Lactobacillus*, *Streptococcus* or *Bifidobacterium* were screened for peptidase activity in the culture supernatant capable to degrade the 33-mer peptide LQLQPFPQPQLPYPQPQLPYPQPQLPYPQPQPF (SEQ ID NO: 1) that is involved in coeliac disease.

The initially selected strains with this ability all belonged to the genus *Lactobacillus* and *Streptococcus*. Subsequently they were then screened for their ability to survive the gastro-intestinal tract and for the stability of the supernatant peptidase activity under gastro-intestinal tract, i.e. their ability to reach and still have an active 33-mer peptide degrading peptidase activity at the site of action for coeliac disease being the small intestine.

Subsequently the selected strains were tested for their ability to degrade other peptides assumed to be involved in coeliac disease, namely a 20-mer from α-gliadin QQLPQPQQPQQSPFQQQRPF (SEQ ID NO: 2) and 13-mer from A-gliadin, LGQQQPFPPQQPY (SEQ ID NO: 3).

Surprisingly it was found that the 33-mer peptide was slowly degraded under conditions mimicking the human digestive tract and that a 18-mer peptide breakdown product PQLPYPQPQLPYPQPQPF (SEQ ID NO: 4) emerged which was completely resistant against further degradation by human digestive enzymes. This novel finding enabled an improved further selection, by screening the lactic acid bacterial strains for their capacity to degrade the 18-mer peptide.

From a large number of strains, five single strains and a mixture of two strains were finally selected. These strains degrade the 33-mer gliadin peptide to the highest extent (at least 45%, preferably at least 70%, of said peptide is hydrolyzed in the presence of a culture supernatant of a selected lactic acid bacterial strain or said mixture as described above). Of this selection a sub-selection of three single strains and a mixture of two strains is preferred, since they have the highest resistance to gastrointestinal conditions, produce a high peptidase activity stable under gastro-intestinal conditions and degrade also the 20-mer, and the 13-mer peptides involved in coeliac disease and also degrade the resistant 18-mer peptide, which was formed from the 33-mer.

The culture supernatant (fermented medium) of the following strains of lactic acid bacteria strains were found to be most efficient in degrading the peptides involved in coeliac disease:

strain DN_114001, being *Lactobacillus casei*, deposited according to the Budapest Treaty at CNCM (Collection Nationale de Cultures de Microorganisms, 25 Rue du Docteur Roux, Paris) under number I-1518 on Jan. 23, 1995. Detailed characteristics of this strain are disclosed in PCT Application WO 96/20607;

strain DN_114077, *Lactobacillus casei* deposited according to the Budapest Treaty at CNCM under number I-4270 on Dec. 16, 2009. This strain was identified as belonging to *L. casei* on the basis of both PCR typing and biochemical activity on API 50 CHL kit (Biomerieux, France). According to the Api 50CHL results the I-4270 strain ferments the following sugars and alcohols: ribose, galactose, glucose, fructose, mannose, sorbose, rhamnose (weak reaction), mannitol, sorbitol, alpha-methyl-D glucoside, N-acetyl glucosamine, amygdalin, arbutin, esculin, salicin, cellobiose, maltose lactose, sucrose, trehalose, inulin, melezitose, starch (weak reaction), gentiobiose, turanose, tagatose, L-arabitol, and gluconate;

strain DN_1190118, *Lactobacillus helveticus* deposited according to the Budapest Treaty at CNCM under number I-4279 on Feb. 25, 2010. This strain was identified as belonging to *L. helveticus* on the basis of both PCR typing and biochemical activity on API 50 CHL kit (Biomerieux, france). According to the Api 50CHL results the I-4279 strain ferments the following sugars and alcohols: galactose, glucose, fructose, mannose, N-acetyl glucosamine and lactose;

strain DN_001343, *Streptococcus thermophilus*, deposited according to the Budapest Treaty at CNCM under number I-2776 on Jan. 24, 2002. This strain was identified as belonging to *S. thermophilus* on the basis of both PCR typing and biochemical activity on API 50 CHL kit (Biomerieux, france). According to the Api 50CHL results the I-2776 strain ferments the following sugars and alcohols: glucose, lactose and sucrose;

strain DN_100290, *Lactobacillus bulgaricus*, deposited according to the Budapest Treaty at CNCM under number I-2787 on Jan. 24, 2002. This strain was identified as belonging to *L. bulgaricus* on the basis of both PCR typing and biochemical activity on API 50 CHL kit (Biomerieux, france). According to the Api 50CHL results the I-2787 strain ferments the following sugars and alcohols: glucose, fructose, mannose and lactose;

strain DN_001546 *Streptococcus thermophilus* CNCM I-4269, deposited according to the Budapest Treaty at CNCM on Dec. 16, 2009. This strain was identified as belonging to *S. thermophilus* on the basis of both PCR typing and biochemical activity on API 50 CHL kit (Biomerieux, france). According to the Api 50CHL results the I-4269 strain ferments the following sugars and alcohols: glucose, lactose, and sucrose; and strain DN_1110272 *Lactobacillus delbrueckii* subsp *lactis* deposited according to the Budapest Treaty at CNCM under number I-4280 on Feb. 25, 2010. This strain was identified as belonging to *L. delbrueckii* subsp *lactis* on the basis of both PCR typing and biochemical activity on API 50 CHL kit (Biomerieux, France). According to the Api 50CHL results the I-4280 strain ferments the following sugars and alcohols: galactose, glucose, fructose, mannose, N-acetyl glucosamine, maltose and lactose.

*S. thermophilus* CNCM I-2776 and *L. bulgaricus* CNCM I-2787 are preferably used together in a mixture, such as a yoghurt starter culture.

In a preferred embodiment, the lactic acid bacterium is selected from the group consisting of *Lactobacillus casei*, *Lactobacillus helveticus*, *Lactobacillus bulgaricus*, *Lactobacillus delbrueckii* subsp *lactis* and *Streptococcus thermophilus*.

In another preferred embodiment, said strain of lactic acid bacterium or mixture of two strain is chosen from the group consisting of *Lactobacillus casei* CNCM I-1518, *Lactobacillus casei* CNCM I-4270, *Lactobacillus helveticus* CNCM I-4279, *Streptococcus thermophilus* CNCM I-4269, *L. delbrueckii* subsp *lactis* CNCM I-4280 and the mixture of *Streptococcus thermophilus* CNCM I-2776 and *Lactobacillus bulgaricus* CNCM I-2787.

Most effective strains under gastro-intestinal conditions and therefore preferred are selected among *Lactobacillus casei* CNCM I-1518 (strain DN_114001), *L. helveticus* CNCM I-4279 (strain DN_1190118), *Lactobacillus delbrueckii* subsp *lactis* CNCM I-4280 (strain DN_1110272); and *S. thermophilus* CNCM I-2776 (strain DN_001343) mixed with *Lactobacillus bulgaricus* CNCM I-2787 (strain DN_100290).

The present invention also encompasses the use of above mentioned strains, but also mutant strains or genetically transformed strains derived from any one of the parent strains still having peptidase activity against the gluten peptides, for anti-coeliac disease purposes. These mutant or genetically transformed strains can be strains wherein one or more endogenous gene(s) of the parent strain has (have) been mutated, for instance to modify some of its metabolic properties (e.g., its ability to ferment sugars, its resistance to acidity, its survival to transport in the gastrointestinal tract, its post-acidification or its metabolite production). They can also be strains resulting from the genetic transformation of the parent strain by one or more gene(s) of interest, for instance in order to give to said strain additional physiological features, or to allow it to express proteins of therapeutic or vaccinal interest that one wishes to administer through said strains.

However, the present invention does not encompass the *Lactobacillus plantarum* strains LB931 (DSM 11918), LB7c (DSM 17853) and LB3e (DSM 17852) and the *Lactobacillus rhamnosus* strain LB21 (NCIMB 40564) disclosed in the PCT Application WO 2007/108763.

Peptidase Activity in Culture Supernatant Against Gluten Peptides:

The peptidase activity, which was located externally of the cells, was highest in cultures wherein the cells were grown to mid-logarithmic phase. This is indicative for the peptidase activity being a part of the primary metabolism. The peptidase activity of some strains was highly stable (at least 25%, preferably at least 30%, peptide degradation), under circumstances mimicking the human gastro-intestinal tract. The peptidase activity results in the cleaving of LQLQPFPQPQLPYPQPQLPYPQPQLPYPQPQPF (SEQ ID NO: 1), QQLPQPQQPQQSPFQQQRPF (SEQ ID NO: 2), LGQQQPFPPQQPY (SEQ ID NO: 3) and the degradation resistant 18-mer peptide breakdown product PQLPYPQPQLPYPQPQPF (SEQ ID NO: 4), preferably the 33-mer peptide of SEQ ID NO: 3 and the 18-mer peptide of SEQ ID NO: 4, as defined above.

The peptidase activity was isolated, purified and sequenced from strain DN_114001, *Lactobacillus casei*, CNCM I-1518 and strain DN_001343, *S. thermophilus*, CNCM I-2776 and surprisingly turned out to be elongation factors. Elongation factor Tu in case of the *Lactobacillus* and elongation factor G in case of the *S. thermophilus*. Elongation factor Tu and G are orthologous genes/proteins. Elongation factors are proteins that facilitate the events of translational elongation, the steps in protein synthesis from the formation of the first peptide bond to the formation of the last one. Bacterial elongation factor Tu can degrade n-termally blocked proteins. Furthermore, elongation factors are surface proteins possessing characteristics of an adhesion factor. Such factors play a role in mucin binding capacity Composition:

The present invention also relates to a composition comprising a lactic acid bacteria or a mixture of two strains of lactic acid bacteria and/or a medium fermented by at least a lactic acid bacteria or a mixture of two strains of lactic acid bacteria, wherein the lactic acid bacteria are selected from the group consisting of the genus *Lactobacillus* and *Streptococcus*. The said lactic acid bacteria, mixture of two strains of lactic acid bacteria and/or fermented medium are capable to degrade the 33-mer peptide LQLQPFPQPQLPYPQPQLPYPQPQLPYPQPQPF (SEQ ID NO: 1), the 20-mer peptide QQLPQPQQPQQSPFQQQRPF (SEQ ID NO: 2), the 13-mer peptide LGQQQPFPPQQPY (SEQ ID NO: 3) and/or the 18-mer peptide PQLPYPQPQLPYPQPQPF (SEQ ID NO: 4), preferably the 33-mer peptide of SEQ ID NO: 3 and the 18-mer peptide of SEQ ID NO: 4, as defined above.

Preferably the lactic acid bacteria of the present invention with the ability to degrade gluten peptides are used to make compositions suitable for enteral administration.

In one embodiment the compositions comprise cells of the lactic acid bacteria as defined above.

Preferably, the composition comprises at least one strain selected from the group consisting of *Lactobacillus helveticus* CNCM I-4279, *L. delbrueckii* subsp *lactis* CNCM I-4280, *Lactobacillus casei* CNCM I-4270, *Streptococcus thermophilus* CNCM I-4269 and a mixture of *S. thermophilus* CNCM I-2776 and *L. bulgaricus* CNCM I-2787, preferably *Lactobacillus helveticus* CNCM I-4279, *L. delbrueckii* subsp *lactis* CNCM I-4280, and a mixture of *S. thermophilus* CNCM I-2776 and *L. bulgaricus* CNCM I-2787.

Preferably said cells are viable. Alternatively the cells may be inactivated, but the inactivation should occur in a mild way, in order not to destroy the enzyme activity to a too high degree. If viable cells are present in said composition, they are preferably present in an amount of $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^8$ cfu/ml.

Viable cells optionally may be present in a composition without the supernatant comprising the peptidase activity. Upon propagation of the cells in the gastro-intestinal tract new peptidase activity will from in situ. Therefore, compositions with cells only still have an anti-gluten activity. Preferably, the bacterial cells can be isolated and added to a composition, for example in the form of dried, frozen or freeze-dried bacterial cells.

In one embodiment the bacterial cells are removed from the composition, but the supernatant comprising the peptidase activity is present in the product. Such a composition is preferably a fermented product from which the bacterial cells have been removed. Suitable ways to remove the bacterial cells are filtration or centrifugation.

In a preferred embodiment both the cells and the supernatant comprising the peptidase activity are present in the composition. Therefore, preferably the lactic acid bacteria of the present invention are used to prepare a fermented product. The fermented product typically has all the extracellular metabolites of the bacteria produced during fermentation, including the gluten peptidase activity, present. Optionally, other strains of lactic acid bacteria may be present. The fermented product can be present in the form of a liquid or present in the form of a dry powder obtained by drying the fermented liquid.

Preferably the fermented product is a fresh product. A fresh product, which has not undergone severe heat treatment steps, has the highest peptidase activity (at least 45%, preferably at least 70%, of a peptide as defined above is hydrolyzed).

Preferably the fermented product is a dairy product, more preferably fermented milk and/or fermented whey. Preferably the nutritional composition is yoghurt, or a fermented milk in set, stirred or drinkable form. Preferably the fermented product is a cheese.

Preferably the fermented product is a fermented vegetable, such as fermented soy, cereals and/or fruits in set, stirred or drinkable forms.

Preferably the present nutritional composition is a baby food, an infant milk formula or an infant follow-on formula. Preferably the present composition is a nutraceutical or a pharmaceutical product, a nutritional supplement or medical food.

The composition may optionally comprise other strains of lactic acid bacteria. These other strains of bacteria may be used to ferment a product, preferably a dairy product.

Method:

The present invention also relates to a method of selecting strains of lactic acid bacteria for use in treatment and/or prevention of coeliac disease comprising the steps of selecting the strains with the capacity of degrading the 33-mer peptide of SEQ ID NO: 1, the 20-mer peptide of SEQ ID NO: 2, the 13-mer peptide of SEQ ID NO: 3 and/or the 18-mer peptide of SEQ ID NO: 4, preferably the the 18-mer peptide of SEQ ID NO: 4, when at least 45%, preferably at least 70% of said peptides is hydrolyzed in the presence of a culture supernatant of said strains.

In an embodiment of said method, it further comprises the step of selecting the strains wherein the capability to degrade the 33-mer peptide of SEQ ID NO: 1, the 20-mer peptide of SEQ ID NO: 2, the 13-mer peptide of SEQ ID NO: 3 and/or the 18-mer peptide of SEQ ID NO: 4 is stable (i.e. more than 25%, preferably more than 30%, of said peptide is degraded) at pH between 4 and 6, preferably at pH 5 and/or stable (i.e. more than 25%, preferably more than 35% of said peptides are degraded) in the presence of digestive enzymes selected from the group consisting of lysozyme, pepsin, chymotrypsin and trypsin.

Example 1: Screening of Supernatants of Lactic Acid Bacteria for the Ability to Degrade the 33-Mer of SEQ ID NO: 1

34 *Lactobacillus*, 10 *Streptococcus* and 3 *Bifidobacterium* strains were selected and their capacity to produce a proteolytic acitivity with capacity to degrade the 33-mer peptide LQLQPFPQPQLPYPQPQLPYPQPQLPYPQPQPF (SEQ ID NO: 1) from α2-gliadin (which is assumed to be responsible of celiac disease) was evaluated.

All of the included micro-organisms were grown both in a general and specific medium.

For *Lactobacillus* strains, the general medium MRS (20 g/l dextrose, 10 g/l peptone, 8 g/l meat extract, 5 g/l sodium acetate, 2 g/l dipotassium phosphate, 2 g/l ammonium citrate, 1 ml Tween 80, 0.2 g/l magnesium sulphate, 0.05 g/l manganese sulphate) was used and the specific medium YGBLP (10 g/l peptone, 8 g/l meat extract, 3 g/l yeast extract, 2.5 g/l monopotassium sulphate, 2.5 g/l dipotassium phosphate, 0.2 g/l magnesium sulphate, 0.05 g/l manganese sulphate, 5 g/l glucose, 5 g/l lactose) was used.

For *Streptococcus* strains the general medium Elliker (5 g/l dextrose, 20 g/l tryptone, 5 g/l sucrose, 1.5 g/l sodium acetate, 2.5 g/l gelatine, 0.5 g/l ascorbic acid, 5 g/l yeast extract, 5 g/l lactose, 4 g/l sodium chloride) and specific medium BHI (12.5 g/l calf brain infusion solids, 5 g/l beef heart infusion solids, 10 g/l proteose peptone, 2 g/l glucose, 5 g/l sodium chloride, 2.5 g/l disodium phosphate) were used.

For *Bifidobacterium* strains were grown in a general medium consisting of MRS with cysteine (0.5 g/l) and in the specific *Bifidobacterium* sp media (10 g/l casein peptone, 5 g/l meat extract, 5 g/l yeast extract, 10 g/l glucose, 1 ml Tween 80, 3 g/l dipotassium phosphate and cysteine 0.5 g/l).

The culture temperature chosen was 25° C. and 37° C. for *Lactobacillus* strains and 37° C. for *Streptococcus* and *Bifidobacterium* strains. The growth was under aerobic and under anaerobic conditions. The supernatants obtained after 5 min centrifugation at 10.000 rpm were used for the in vitro 33-mer peptide degradation assay. Supernatants from growth in general and specific medium were obtained in logarithmic and stationary phase cultures in order to screen for degrading activity as a result of primary and secondary metabolism.

The 33-mer peptide degradation assay was carried out by enzymatic proteolysis activity present in the culture supernatants of the selected microorganisms. The reaction was carried out with 114 µl PBS (100 mM, pH 7.3), 12 µl 33-mer peptide (1.7 mM) which was synthesized by and obtained from GENSCRIPT (Pscataway, USA) and 24 µl culture supernatant during 48 hours at 37° C. Subsequently, the samples were boiled, filtered through 0.45 µm and analysed by high-performance liquid chromatography equipped with a Photodiode Array detector.

The quantification of the residual 33-mer peptide was evaluated by means of HPLC with a $C_{18}$ column from Waters. The peptide detection was done at $220_{nm}$ and 35° C. The solvents used were mili-Q water with TFA (0.1%) and acetonitrile with TFA (0.1%).

Table 1 below discloses the results of the screening of the supernatants. It turned out that especially supernatants of strains belonging to the genera *Lactobacillus* and *Streptococcus* were capable of degrading the peptide and that cells grown in the logarithmic phase were more efficient in peptide degradation than cells grown in the stationary phase. Furthermore, cells grown on the general medium were in most cases better able to degrade the 33-mer than cells grown on specific medium.

TABLE 1

Percentage of 33-mer peptide LQLQPFPQPQLPYPQPQLPYPQPQLPYPQPQPF (SEQ ID NO: 1) degradation by culture supernatants from *Lactobacillus*, *Bifidobacterium* and *Streptococcus* strains grown to logarithmic phase culture and stationary phase culture on specific or general medium.

| Strain | | Growth Phase | | | |
|---|---|---|---|---|---|
| | | logaritmic | | stationary | |
| | | Growth Medium | | | |
| | | general | specific | general | specific |
| *Lactobacillus* | | | | | |
| P02431 | C3 | — | — | 52.4 ± 1.5 | 30.3 ± 9.6 |
| | F2 | — | — | 58.5 ± 2.0 | 38.8 ± 12.4 |
| | A3 | — | — | 43.3 ± 2.4 | 53.6 ± 10.8 |
| | G2 | — | — | 3.9 ± 10.1 | 0.0 ± 0.0 |
| | E1 | 76.5 ± 1.9 | 15.6 ± 2.3 | 32.1 ± 10.4 | 0.0 ± 0.0 |
| | C7 | 74.6 ± 1.4 | 15.6 ± 3.0 | 39.7 ± 3.3 | 9.6 ± 1.6 |
| | C1 | 81.9 ± 1.1 | 33.1 ± 15.0 | 43.7 ± 1.1 | 14.3 ± 4.9 |
| | D1 | 36.5 ± 3.3 | 22.6 ± 3.0 | 45.9 ± 0.3 | 7.4 ± 8.6 |
| | F1 | 78.0 ± 0.2 | 10.5 ± 3.8 | 47.0 ± 2.6 | 10.0 ± 1.2 |
| | G1 | 80.9 ± 0.5 | 17.2 ± 1.4 | 44.2 ± 2.0 | 6.5 ± 5.1 |
| | A2 | 77.4 ± 1.2 | 12.4 ± 3.2 | 32.8 ± 1.0 | 0.0 ± 0.0 |
| P02503 | A1 | 72.5 ± 0.0 | 19.3 ± 4.1 | 25.6 ± 5.7 | 8.3 ± 2.0 |
| | H3 | 81.6 ± 3.7 | 16.9 ± 6.9 | 39.7 ± 3.0 | 0.0 ± 0.0 |
| | C4 | 66.1 ± 4.2 | 10.1 ± 1.3 | 27.8 ± 3.1 | 0.3 ± 0.9 |
| | C2 | 76.9 ± 2.4 | 19.3 ± 4.4 | 7.6 ± 3.1 | 0.0 ± 0.0 |
| | A3 | 87.5 ± 1.0 | 15.9 ± 1.4 | 18.3 ± 1.1 | 0.0 ± 0.0 |
| | B3 | 58.7 ± 2.7 | 17.3 ± 3.9 | 14.1 ± 1.2 | 0.0 ± 0.0 |
| | E1 | 74.9 ± 0.8 | 10.1 ± 2.9 | 11.0 ± 2.5 | 0.0 ± 0.0 |
| | A2 | 55.1 ± 1.9 | 17.1 ± 5.5 | 19.2 ± 2.1 | 2.9 ± 7.3 |
| | F2 | 59.2 ± 1.3 | 11.6 ± 0.4 | 34.7 ± 2.3 | 2.0 ± 3.5 |
| | H2 | 73.7 ± 0.4 | 19.0 ± 2.7 | 35.6 ± 2.6 | 0.5 ± 4.4 |
| P02535 | G1 | 49.4 ± 1.4 | — | 34.7 ± 2.3 | 2.0 ± 3.5 |
| | D5 | 10.7 ± 1.5 | 0.7 ± 12.5 | 35.6 ± 2.6 | 0.5 ± 4.4 |
| | H3 | — | — | 0.0 ± 1.4 | 8.4 ± 0.7 |
| | A1 | 5.0 ± 8.0 | 5.9 ± 2.3 | 29.7 ± 3.2 | 11.5 ± 3.2 |
| P02523 | H3 | 64.9 ± 6.9 | 18.2 ± 7.0 | 27.8 ± 1.3 | — |
| | B3 | 65.3 ± 1.7 | 28.7 ± 3.3 | 32.3 ± 2.1 | 4.2 ± 0.2 |
| | F3 | 63.6 ± 5.5 | 35.8 ± 0.0 | 28.9 ± 0.1 | 0.1 ± 1.5 |
| | A4 | 71.7 ± 0.0 | 24.4 ± 2.6 | 25.8 ± 1.1 | 0.0 ± 3.2 |
| | B7 | 3.6 ± 15.4 | 11.5 ± 0.9 | 24.5 ± 0.1 | 0.2 ± 4.8 |
| P02445 | B1 | 71.9 ± 1.9 | 27.1 ± 5.1 | 28.7 ± 3.9 | 9.0 ± 2.5 |
| | H7 | 73.2 ± 0.0 | 8.2 ± 1.9 | 73.5 ± 0.6 | 3.0 ± 5.7 |
| | A8 | 56.4 ± 22.3 | 10.3 ± 6.6 | 43.1 ± 2.9 | 0.7 ± 4.1 |
| | C8 | 54.2 ± 26.3 | 2.1 ± 3.4 | 42.9 ± 1.9 | 6.5 ± 5.3 |
| | E10 | 62.6 ± 1.0 | 27.7 ± 3.6 | 0.0 ± 3.1 | 27.0 ± 4.9 |
| | B9 | 0.0 ± 0.0 | 26.3 ± 3.0 | 0.0 ± 1.9 | 22.4 ± 2.3 |
| | F8 | 27.4 ± 5.4 | 0.0 ± 0.2 | 0.0 ± 2.3 | 22.7 ± 4.5 |
| | G8 | 0.0 ± 4.1 | 19.0 ± 2.4 | 4.3 ± 12.7 | 21.6 ± 4.5 |
| *Bifidobacterium* | | | | | |
| P02495 | D1 | 64.2 ± 6.9 | — | — | — |
| | H1 | 65.9 ± 7.4 | — | — | — |
| | F5 | 48.6 ± 8.4 | 21.32 ± 4.22 | 26.1 ± 2.9 | 64.5 ± 12.2 |
| | A4 | 32.2 ± 7.8 | 23.56 ± 8.59 | 2.9 ± 23.1 | 1.6 ± 14.9 |
| | G5 | 15.8 ± 16.3 | 15.65 ± 1.21 | 24.8 ± 5.0 | 25.1 ± 4.7 |
| *Streptococcus* | | | | | |
| P02654 | G1 | 81.1 ± 3.5 | 53.4 ± 15.3 | 73.7 ± 0.4 | 71.8 ± 7.5 |
| P02646 | A7 | 80.9 ± 21.2 | 45.2 ± 3.2 | 78.6 ± 2.5 | 50.4 ± 15.6 |
| | A9 | 93.8 ± 0.9 | 44.6 ± 3.3 | 78.4 ± 1.1 | 76.9 ± 20.5 |
| | E1 | 84.6 ± 0.0 | 44.0 ± 1.9 | 77.9 ± 2.9 | 62.7 ± 0.9 |
| | B3 | 85.3 ± 0.7 | 47.4 ± 2.2 | 79.8 ± 0.3 | 40.9 ± 3.0 |
| P02638 | H7 | 87.5 ± 2.0 | 49.7 ± 2.8 | 62.9 ± 0.7 | 86.7 ± 3.2 |
| | F9 | 82.4 ± 3.7 | 93.6 ± 9.1 | 57.3 ± 3.0 | 58.1 ± 6.3 |
| | B10 | 82.9 ± 1.2 | 70.4 ± 0.3 | 58.5 ± 0.9 | 46.0 ± 5.4 |
| | D10 | 82.1 ± 1.7 | 66.3 ± 0.2 | 51.2 ± 5.4 | 35.3 ± 4.4 |
| | G10 | 76.6 ± 3.3 | 83.1 ± 1.0 | 59.3 ± 0.7 | 49.9 ± 1.6 |

Example 2: Screening of Selected Cells and Supernatants of Lactic Acid for Resistance Against the Gastro-Intestinal Tract The strains most efficient in 33-mer degradation, strain P02503 A1, P02503 A3, P02431 C1, P02445 H7, P02638 H7, P02646 A9 were selected and also a mixture of P02638 F9/P02523 A4, was selected as a typical yogurt symbiosis. They were identified on the basis of both PCR typing and biochemical activity on API 50 CHL kit (Biomerieux, France).

P02503 A1 is strain DN_114001, *Lactobacillus casei*, deposited at CNCM under number I-1518 on Jan. 23, 1995.

P02431 C1 is strain DN_1190118, *Lactobacillus helveticus* deposited at CNCM under number I-4279 on Feb. 25, 2010.

P02445 H7 is strain DN_1110272, *Lactobacillus delbrueckii* subsp *lactis* deposited at CNCM under number I-4280 on Feb. 25, 2010.

P02638 F9 is strain DN_001343, *Streptococcus thermophilus*, deposited at CNCM under number I-2776 at Jan. 24, 2002.

P02523 A4 is strain *Lactobacillus bulgaricus* DN_100290 deposited at CNCM under number I-2787 at Jan. 24, 2002. These two strains are used in a mixture as a yoghurt starter culture.

P02503 A3 is strain DN_114077 *Lactobacillus casei* deposited at CNCM under number I-4270 on Dec. 16, 2009.

P02646 A9 is strain DN_001546 *Streptococcus thermophilus* deposited at CNCM under number I-4269 on Dec. 16, 2009.

The resistance of these strains against a low pH and against digestive enzymes was tested. Strains should be selected which are resistant against a low pH and resistant against digestive enzymes, since such strains are able to survive the passage though the mouth, stomach and the intestinal tract, which is a prerequisite in order to exert the anti-coeliac disease effects in vivo. Not only the cells, but also the supernatants comprising the peptidase activity against the 33-mer peptide were tested for their resistance against low pH and digestive enzymes. Cells were grown for 17 h and collected by centrifugation (4000 rpm, 5 min) and resuspended in PBS buffer. For the pH resistance assay, the buffer had pH 2, 3, 4, 5, 6, 7 or 8. The results are shown in Table 2. Only results of pH 3 and 5 are shown which are typical for the pH resistance. For resistance against digestive enzymes cells were resuspended in PBS buffer at pH 3 (pepsin), pH 7 (chymotrypsin and trypsin) and pH 6 (lysozyme). Cells were incubated for 2 h at 37° C., except in case of lysozyme. When lysozyme was tested cells were incubated for 5 min.

In case of supernatant testing, cells were cultured for 17 h, and cells were removed by centrifugation (4000 rpm). The supernatant was lyophilized and resuspended under the same conditions as described above for the cells.

TABLE 2

Resistance of lactic acid bacteria cells and the peptidase activity of culture supernatants against low pH and against the presence of digestive enzymes.

| Strain | | pH 5 | pH 3 | Lysozyme | Pepsin | Chymotrypsin | Trypsin |
|---|---|---|---|---|---|---|---|
| P02503 A1 | Cells[a] | 100 | 91 | 100 | 100 | 100 | 95 |
| | Supernatant[b] | 34.9 | 42.7 | 36.7 | 63.2 | 47.1 | 56.2 |
| P02503 A3 | Cells | 100 | 100 | 100 | 26.2 | 42.6 | 24.9 |
| | Supernatant | nd[c] | nd | nd | nd | nd | nd |
| P02431 C1 | Cells | 86 | 81 | 65.9 | 101 | 63.8 | 38.2 |
| | Supernatant | 36.1 | 33.1 | 69.9 | 67.8 | 59.1 | 56.2 |
| P02445 H7 | Cells | 80 | 47 | 4.5 | 62 | 88.1 | 99.1 |
| | Supernatant | 32.6 | 35.7 | 61.2 | 60.1 | 37.4 | 86.4 |
| P02638 H7 | Cells | 3 | 4 | 42.6 | 3.0 | 3.3 | 4.0 |
| | Supernatant | nd | nd | nd | nd | nd | nd |
| P 02646 A9 | Cells | 3 | 3 | 2.0 | 100 | 4.3 | 52.9 |
| | Supernatant | nd | nd | nd | nd | nd | nd |
| P 02638 F9/ | Cells | 100 | 97 | 29.1 | 66.7 | 82.7 | 100 |
| P02523 A4 | Supernatant | 39.2 | 39.3 | 85.6 | 55.5 | 54.0 | 81.8 |

[a]viability in %.
[b]Residual 33-mer degrading activity in %.
[c]nd: not determined Most selected cells and supernatants show a high survival percentage under low pH conditions and in presence of digestive enzymes. Regarding culture supernatants, most of them were able to degrade the 33-mer peptide in vitro.

Example 3: Screening of Supernatants of Selected Strains for the Ability to Degrade the 20-Mer of SEQ ID NO: 2 and 13-Mer of SEQ ID NO: 3

Subsequently a screening was performed to determine the ability to degrade other peptides involved with coeliac disease, namely the 20-mer and the 13-mer.

In the same way as in Example 1, the capacity of different supernatants (P02503 A1, P02431 C1, P02445 H7 and the mixture P02523 A4-P02638 F9 to degrade other peptides involved in celiac disease as 20-mer from α-gliadin (QQLPQPQQPQQSPFQQQRPF) and 13-mer from A-gliadin (LGQQQPFPPQQPY) were assayed. A high degradation of both samples with the selected strains was detected (Table 3). These data underline the important role of the proteolytic activity of the culture supernatants of the selected strains not only the principal peptide related with celiac disease but also other peptides involves in this disorder.

TABLE 3

Percentage of 13-mer and 20-mer peptide degradation by the selected strains

| Strain | 13-mer | 20-mer |
| --- | --- | --- |
| P02503 A1 | 74.86 ± 1.31 | 61.08 ± 2.22 |
| P02431 C1 | 52.46 ± 0.00 | 50.54 ± 0.87 |
| P02445 H7 | 72.05 ± 1.93 | 47.06 ± 0.36 |
| P02523 A4-P02638 F9 | 71.38 ± 1.10 | 63.13 ± 5.22 |

Example 4: Identification of Other More Resistant Peptides Potentially Involved with Celiac Disease Although the 33-mer peptide from α-gliadin as a principal contributor to gluten immunotoxicity and responsible of celiac disease, an enzymatic in vitro digestion model of an in vivo digestive tract was developed for mimicking the physiological conditions to check and certify that the peptide was not degraded throughout the gastro-intestinal tract by the digestive process. Pepsin, pancreatin and bile concentrations were optimized using an experimental design (Granato-Lorencio, et al (2007). J. Agric. Food Chem., 55, 6387-6394).

By means of a high-performance liquid chromatography it was observed that the 33-mer peptide LQLQP-FPQPQLPYPQPQLPYPQPQLPYPQPQPF was completely degraded at the end of the process, which is representative for the distal part of the small intestine. Surprisingly, by mass/mass spectrometry (MS/MS) the presence of a 18-mer peptide (PQLPYPQPQLPYPQPQPF) as a major degradation product was identified, which had the capacity to pass through the digestive tract unchanged, without further degradation.

For this reason the supernatants were also selected for their ability to degrade the 18-mer peptide.

The results are shown in Table 4.

TABLE 4

Ability to degrade the 18-mer peptide

| Strain | Degradation 18-mer % |
| --- | --- |
| P02503 A1 | 100 |
| P02638 F9 | 100 |

Example 5: Purification and Characterization of the Protease Able to Degrade the 33-Mer of SEQ ID NO: 1 and 18-Mer Peptide of SEQ ID NO: 4 Involved in Celiac Disease The protease able to degrade in vitro the 33-mer as well as the 18-mer peptide of two selected strains from *Lactobacillus* (P02503 A1) and *Streptococus* (P02638 F9) was purified.

Four litres of the selected *Lactobacillus* A1 and *Streptococcus* F9 strains were grown without stirring in MRS cysteine and BHI media, respectively, and the supernatant enzyme having the proteolytic activity was purified to homogenity by ammonium sulphate precipitation. The residual ammonium sulphate which was bound to the protein was dialysed against a buffer low in salt concentration.

Purification of A1 and F9 proteases was accomplished by anion exchange chromatography with HiPrep 16/10 Q XL column in a chromatography system AKTA Explorer. Fractions were desorbed with Tris-HCl 20 mM, pH 8.5, $CaCl_2$ 5 mM buffer with a linear gradient from 0 to 1M NaCl and were then tested in vitro at 37° C. during 48 hours to evaluate the protease activity against 33-mer and 18-mer peptides.

The fractions with protease activity against the 33-mer and the 18-mer peptide were further purified on a hydrophobic interaction chromatography (HIC) with HiPrep 16/10 Phenyl FF (high sub) column and fractions were desorbed with 100 mM sodium phosphate buffer pH7 with a linear gradient from 1.5 to 0 M $(NH_4)_2SO_4$. All hydrophobic interaction chromatography fractions were assayed in vitro and those containing protease activity were pooled and isolated using a 10 kDa molecular weight cut-off membrane (Amicon Ultra, Millipore). 1-D native sodium dodecyl sulfate polyacrylamide gel electrophoresis (SDS-PAGE) was used for the separation of individual proteins and the purified A1 *Lactobacillus* and F9 *Streptococcus* enzymes were sequenced and identified as "elongation factor Tu" from *Lactobacillus casei* and "elongation factor G" from *Streptococcuss thermophilus* with a molecular mass of 45.3 kDa and 76.6 kDa respectively. Elongation factor Tu and In the characterization and kinetic parameters of "elongation factor Tu" enzyme from A1 *Lactobacillus* and "elongation factor G" enzyme from F9 *Streptococcus*, it was found that their maximum protease activity against 18-mer peptide was at pH 7.3 and 37° C. and micromolar concentrations of $Zn^{2+}$ caused an inhibition of 18-mer proteolysis. $K_m$ and $V_{max}$ values for A1 *Lactobacillus* protease were 0.643 mg 18-mer peptide/ml and 1.272 mg 18-mer peptide/ml respectively and $K_m$ and $V_{max}$ values for F9 *Streptococcus* protease were 0.794 mg 18-mer peptide/ml and 1.5022 mg 18-mer peptide/ml respectively.

The invention claimed is:

1. A fermented dairy composition comprising by at least one lactic acid bacteria strain selected from the group consisting of *Lactobacillus helveticus* CNCM I-4279, *Lactobacillus delbrueckii* subsp *lactis* CNCM I-4280, *Lactobacillus casei* CNCM I-4270, *Streptococcus thermophilus* CNCM I-4269 and a mixture of *Streptococcus thermophilus* CNCM I-2776 and *Lactobacillus bulgaricus* CNCM I-2787, said composition comprising $10^5$ to $10^{13}$ cfu per g of said lactic acid bacteria strain, and further comprising a protein elongation factor for degradation of a 33-mer peptide of SEQ ID NO: 1, a 20-mer peptide of SEQ ID NO: 2, a 13-mer peptide of SEQ ID NO: 3 and/or a 18-mer peptide of SEQ ID NO: 4 said factor being a product of fermentation.

2. The fermented dairy composition of claim 1 wherein the composition is a liquid product.

* * * * *